US00PP31077P3

(12) United States Plant Patent
Meilland

(10) Patent No.: US PP31,077 P3
(45) Date of Patent: Nov. 19, 2019

(54) BEDDING ROSE PLANT NAMED 'MEIZYGGLIE'

(50) Latin Name: *Rosa hybrida*
Varietal Denomination: MEIZYGGLIE

(71) Applicant: The Conard-Pyle Company, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/932,688

(22) Filed: Apr. 10, 2018

(65) Prior Publication Data

US 2019/0313560 P1 Oct. 10, 2019

(51) Int. Cl.
*A01H 5/02* (2018.01)
*A01H 6/74* (2018.01)

(52) U.S. Cl.
USPC ..... Plt./180
CPC ..... *A01H 6/749* (2018.05)

(58) Field of Classification Search
USPC ..... Plt./108, 139, 140, 150, 151
CPC ..... A01H 5/02; A01H 5/0222; A01H 5/00; A01H 6/74; A01H 6/749
See application file for complete search history.

(56) References Cited

U.S. PATENT DOCUMENTS

PP6,895 P 7/1989 Meilland
PP16,202 P2 1/2006 Radler

OTHER PUBLICATIONS

Monrovia 2019 Grace N' Grit Red Shrub Rose, retrieved on Mar. 19, 2019, retrieved from the Internet at https://www.monrovia.com/plant-catalog/plants/6219/grace-n-grit-red-shrub-rose/, 2 pp. (Year: 2019).*

Monrovia Releases Record Breaking Number of New Plants in 2018, retrieved on Mar. 19, 2019, retrieved from the Internet at https://www.globenewswire.com/news-release/2017/11/01/1172660/0/en/Monrovia-Releases-Record-Breaking-Number-of-New-Plants-in-2018.html, 2 pp. (Year: 2017).*

* cited by examiner

*Primary Examiner* — June Hwu
(74) *Attorney, Agent, or Firm* — Buchanan Ingersoll & Rooney PC

(57) ABSTRACT

A new and distinct variety of Bedding Rose plant, herein referred to by its cultivar name, 'MEIZYGGLIE', is provided which forms very abundantly on a nearly continuous basis attractive, cup-shaped, intense red colored blossoms. Attractive, glossy, very dense foliage is formed, which contrasts beautifully with the blossoms. The growth habit is vigorous. The disease tolerance is very good, particularly against rust and Black Spot. The new variety is well suited for proving attractive ornamentation in the landscape.

1 Drawing Sheet

Figures 1, 2, 3, 4, 5, 6, 7, 8, 9, 10, 11, 12, 13, 14, 15, 16:
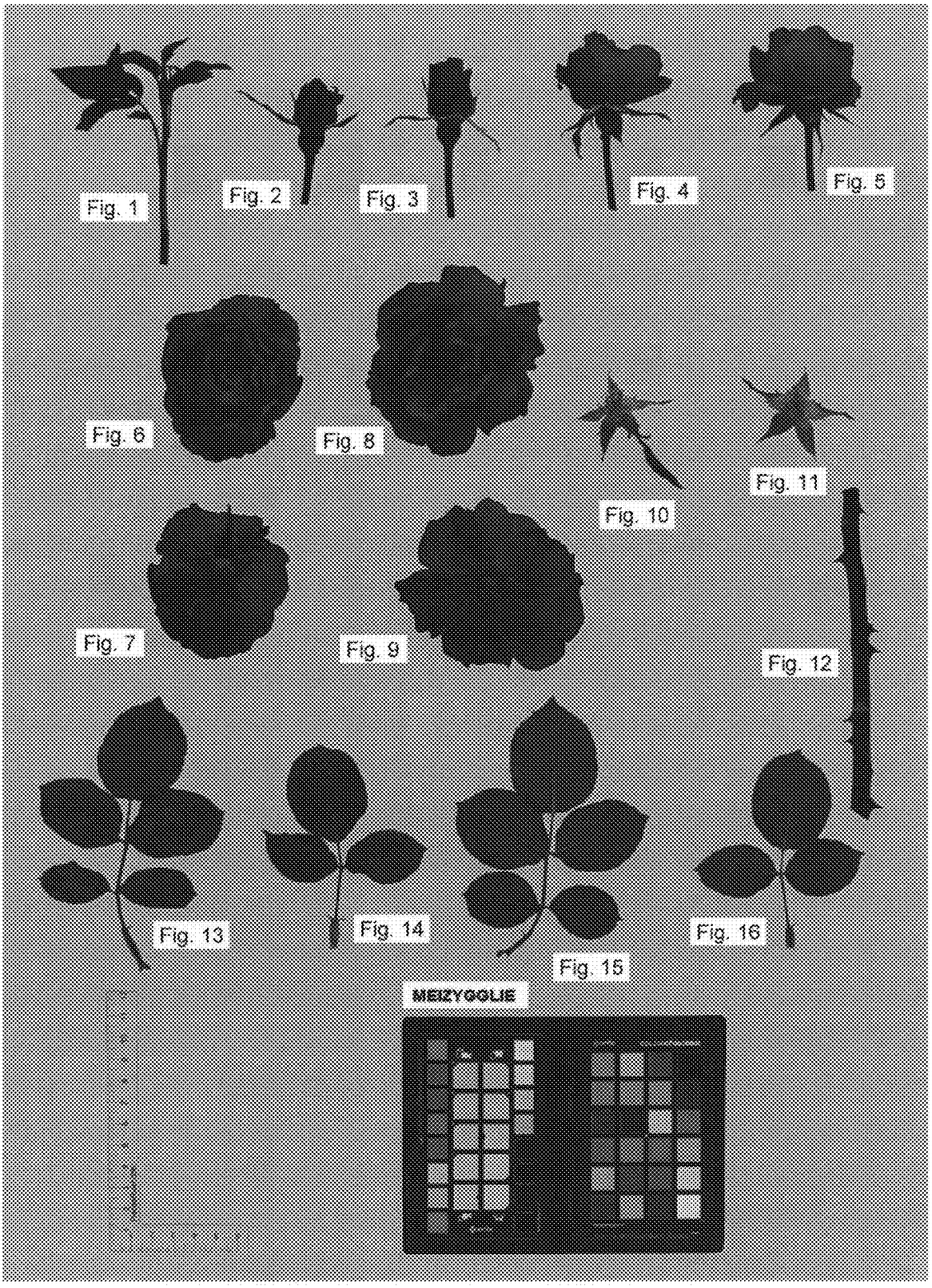

Botanical/commercial classification:
Latin name—*Rosa hybrida.*
Common name—Bedding Rose Plant.
Varietal denomination: 'MEIZYGGLIE'.

SUMMARY OF THE INVENTION

The new variety of *Rosa hybrida* Bedding Rose plant was created by artificial pollination wherein two parents were crossed which previously had been studied in the hope that they would contribute the desired characteristics. The female parent (i.e., the seed parent) was the product of the cross between the 'MEIVILDO' variety (U.S. Plant Pat. No. 6,895) and the 'MME VERBELEN' variety (non-patented in the United States). The male parent (i.e., the pollen parent) was the 'RADTKO' variety (U.S. Plant Pat. No. 16,202).

The parentage of the new variety can be summarized as follows:

('MEIVILDO' x 'MME VERBELEN') x 'RADTKO'

The seeds resulting from the above pollination were sown and small plants were obtained which were physically and biologically different from each other. Selective study resulted in the identification of a single plant of the new variety.

It was found that the new variety of Bedding Rose plant of the present invention possesses the following combination of characteristics:

(a) very abundantly and nearly continuously forms attractive, cup-shaped, intense red colored blossoms,
(b) forms attractive, very dense, glossy foliage,
(c) exhibits very good tolerance to diseases, particularly against rust and Black Spot,
(d) displays a vigorous growth habit, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEIVILDO' variety (i.e., parent of the seed parent) displays deep pink colored blossoms and the 'RADTKO' variety (i.e., the pollen parent) displays dark pink colored blossoms, whereas the new variety displays red colored blossoms. The 'MME VERBELEN' variety (i.e., parent of the seed parent) is a hybrid tea rose plant, whereas the new variety is a bedding rose plant. Moreover, the new variety can be readily distinguished from non-parental related similar varieties. For example, the 'Meimacota' variety (U.S. Plant Pat. No. 30,537) displays flowers which are larger in size compared to the new variety.

The new variety has been found to undergo asexual propagation in Le Cannet des Maures, France by a number of routes, including budding, eye budding grafting, and the use of cuttings, including softwood, hardwood, or semi-hardwood cuttings. Asexual propagation by the above-mentioned techniques in Le Cannet des Maures, France has shown that the characteristics of the new variety are stable and are strictly transmissible by such asexual propagation from one generation to another. Accordingly, the new variety undergoes asexual propagation in a true-to-type manner.

The new variety has been named 'MEIZYGGLIE'.

BRIEF DESCRIPTION OF THE PHOTOGRAPH

The accompanying photographs show as nearly true as it is reasonably possible to make the same, in a color illustration of this character, typical specimens of the plant parts of the new variety. The rose plants of the new variety were approximately two years of age and were observed during July while budded on their own roots and growing outdoors at Le Cannet des Maures, Var, France. Standard color information and dimensions in centimeters are included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening of the petals.

FIG. 5—illustrates a specimen of a flower in the course of opening.

FIG. 6—illustrates a specimen of a flower in the course of opening—plan view—obverse.

FIG. 7—illustrates a specimen of a flower in the course of opening—plan view—reverse FIG. 8—illustrates a specimen of a fully open flower—plan view—obverse.

FIG. 9—illustrates a specimen of a fully open flower—plan view—reverse.

FIG. 10—illustrates a specimen of a floral receptacle showing arrangement of the stamens and pistils.

FIG. 11—illustrates a specimen of a floral receptacle showing arrangement of the pistils (stamens removed).

FIG. 12—illustrates a specimen of a flowering stem.

FIG. 13—illustrates a specimen of a leaf with 5 leaflets—plan view—upper surface.

FIG. 14—illustrates a specimen of a leaf with 3 leaflets—plan view—upper surface.

FIG. 15—illustrates a specimen of a leaf with 5 leaflets—plan view—under surface.

FIG. 16—illustrates a specimen of a leaf with 3 leaflets—plan view—under surface.

DETAILED BOTANICAL DESCRIPTION

The chart used in the identification of the colors is that of The Royal Horticultural Society (R.H.S. Color Chart, edition 2001), London, England. The terminology which precedes reference to the chart has been added to indicate the corresponding color in more common terms. The description is based on the observation of two-year-old specimens of the new variety during July while budded on their own roots and growing outdoors at Le Cannet des Maures, Var, France.

Class: Bedding Rose Plant.

Plant:

*Habit*.—Bushy, vigorous.

*Height*.—Near 70 cm on average in container.

*Spread*.—Near 65 cm on average in container.

Branches:

*Color*.—Young stems: commonly near Yellow-Green Group 146B. Adult wood: commonly between near Yellow-Green Group 146B and near Yellow-Green Group 146C.

*Thorns*.—Configuration on adult stems: slightly curved downward on the upper surface and concave on the under surface. Long prickles — quantity: commonly approximately 10 thorns per 10 cm long adult stem. Long prickles — base shape: oval on adult stems. Long prickles — size: commonly near 0.5 to 0.9 cm in length on average on adult stems. Long prickles — color: commonly near Greyed-Orange Group 175B on adult stems. Long prickles — young stems: none observed. Small prickles (<0.5 cm): none observed.

Foliage:

*General appearance*.—Very dense with a glossy aspect.

*Glossiness intensity of the upper surface of leaf*.—Medium.

*Number of leaflets*.—3, 5, and 7; most often 5 or 7.

*Terminal leaflet*.—Length: approximately 4.8 cm on average. Width: approximately 3.5 cm on average.

5-*leaflet leaf*.—Length: approximately 11 cm on average. Width: approximately 8 cm on average.

*New foliage*.—Upper surface color: commonly near Yellow-Green Group 147B more or less suffused with Greyed-Purple Group 185A. Under surface color: commonly near Yellow-Green Group 147C more or less suffused with Greyed-Purple Group 185A.

*Adult foliage*.—Upper surface color: commonly near Yellow-Green Group 147A. Under surface color: commonly near Yellow-Green Group 147B.

Leaflets:

*Shape*.—Tip: cuspidate. Base: rounded.

*Texture*.—Leathery.

*General appearance*.—Oval.

*Edge*.—Slightly denticulate.

*Serration*.—Small and single.

*Petiole rachis*.—Color of upper surface: commonly near Yellow-Green Group 147C. Color of under surface: commonly near Yellow-Green Group 147B.

*Petioles*.—Upper surface: no glandular. Under surface: few prickles. Color of upper surface: commonly near Yellow-Green Group 147B. Color of under surface: commonly near Yellow-Green Group 147C. Petiole length of terminal leaflet: commonly near 2.1 cm on average.

*Stipules*.—General appearance: adnate, pectinate and narrow. Length: approximately 1.2 cm on average. Width: approximately 0.3 cm on average. Color of upper surface: commonly near Yellow-Green Group 147C. Color of under surface: commonly near Yellow-Green Group 147B.

Inflorescence:

*Number of flowers per stem*.—Generally between 1 and 9 flowers per stem.

*Inflorescence size*.—Height is approximately 11.5 cm on average, when 2-9 flowers are present; and width is approximately 15 cm on average when 2-9 flowers are present.

*Pedicel*.—Length is approximately 4.5 cm on average, diameter is approximately 0.25 cm on average, texture is prickly, and color is commonly near Green Group 143C with near Greyed-Purple Group 187D on it.

*Bud*.—Shape: conical. Size: small. Length: approximately 1.6 cm on average. Width: approximately 1.5 cm on average. Color as calyx breaks: Upper surface: commonly near Red Group 45A to near Red Group 46A. Under surface: commonly near Red Group 53B.

*Sepals*.—Length: approximately between 1.1 cm on average. Width: approximately near 0.4 cm on average. Shape: with little extensions (approximately 1.0 cm on average). At the top: narrow and longish. At the base: flat to downward for open flowers. Upper surface: Texture: tomentous. Color: commonly near Yellow-Green Group 148C. Under surface: Texture: smooth. Color: commonly near Yellow-Green Group 147C.

*Receptacle*.—Color: commonly near Yellow-Green Group 147C. Length: approximately 0.9 cm on average. Width: approximately 0.6 cm on average. Surface: smooth. Shape: funnel shaped.

*Peduncle*.—Length: approximately near 4.1 cm on average. Width: approximately 0.3 cm on average. Surface: glandular. Color: commonly near Yellow-Green Group 147C.

*Flower*.—Average diameter when fully open: approximately 7 to 8 cm on average. Height: approximately 3.5 cm on average. Lastingness: approximately 2 weeks on average. Borne: commonly between 1 to 9 flowers per stem. Shape: cup shaped. Number of petals under normal conditions: approximately 18 to 20 petals on average. Shape of the petal: ovoid. Base: obtuse. Top: rounded. Petal undulation: weak. Petal incision: very weak to weak. Petal margin: reflexing of the margin is weak; weak crenated petal margin. Texture of the petal: leathery. Petal length: approximately 2.9 cm on average. Petal width: approximately 2.6 cm on average. Petal arrangement: imbricated without petaloids. Petal drop: petals drop off cleanly before drying. Fragrance: none. Color when opening: Upper surface: commonly near Red Group 45A to near Red Group 46A. Under surface: commonly near Red Group 53B. Color of the open flower: Upper surface: commonly near between Red Group 53B and Red Group 53C, with a small basal spot near Yellow Group 3C mixed with near Yellow-White Group 158C. Under surface: commonly near Red-Purple Group 61C. Color when fading: commonly near Red-Purple Group 63A with near Red-Purple Group 74C on it. Anthers: number is approximately 87 on average, length is approximately 0.1 cm on average, coloration is commonly near Orange Group 26C, and arrangement is regular around styles. Filaments: length is approximately 0.3 cm on average and coloration is commonly near Orange-Red Group 34C. Styles: length is approximately 0.2 cm on average, coloration is commonly near Yellow Group 2C, and number is approximately 42 on average. Stigmas: size is approximately 0.1 cm on average and coloration is commonly near Yellow Group 2C. Pollen: color is commonly near Greyed-Orange Group 168B after 24 hours of drying. Hips: not available at this stage.

Development:

*Vegetation*.—Very strong.

*Blooming*.—Early in the season, very abundant and nearly continuous.

*Tolerance to disease*.—Very good, and particularly against rust (*Phragmidium tuberculatum* and *Phragmidium mucronatum*) and Black Spot (*Diplocarpon rosae*).

*Hardiness*.—USDA Zone 4 to 9.

The new 'MEIZYGGLIE' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Bedding Rose plant characterized by the following combination of characteristics:

(a) very abundantly and nearly continuously forms attractive, cup-shaped, intense red colored blossoms, (b) forms attractive, very dense, glossy foliage, (c) exhibits very good tolerance to diseases, particularly against rust and Black Spot, (d) displays a vigorous growth habit, and (e) is well suited for providing attractive ornamentation; substantially as herein shown and described.

* * * * *

MEIZYGOLIE